United States Patent
Jessop et al.

(10) Patent No.: US 9,277,933 B1
(45) Date of Patent: Mar. 8, 2016

(54) METHOD FOR ULTRASONIC DISSECTION OF TISSUES

(75) Inventors: Israel James Jessop, Annandale, NJ (US); Benjamin T. Kibalo, Columbia, MD (US); Adrian F. Barbieri, Branchburg, NJ (US)

(73) Assignee: LIFECELL CORPORATION, Branchburg, NJ (US)

( * ) Notice: Subject to any disclaimer, the term of this patent is extended or adjusted under 35 U.S.C. 154(b) by 16 days.

(21) Appl. No.: 13/192,023

(22) Filed: Jul. 27, 2011

Related U.S. Application Data

(60) Provisional application No. 61/368,354, filed on Jul. 28, 2010.

(51) Int. Cl.
*A61B 17/32* (2006.01)
*A61B 17/322* (2006.01)

(52) U.S. Cl.
CPC . *A61B 17/320068* (2013.01); *A61B 2017/3225* (2013.01)

(58) Field of Classification Search
CPC .............. A61B 17/320068; A61B 17/22012; A61B 18/14; A61B 17/322; A61N 7/00; A61N 2007/0008
USPC ............... 606/132, 169; 604/22, 542; 601/2
See application file for complete search history.

(56) References Cited

U.S. PATENT DOCUMENTS

| | | | |
|---|---|---|---|
| 6,203,540 B1 * | 3/2001 | Weber .............................. | 606/15 |
| 6,685,657 B2 * | 2/2004 | Jones .............................. | 601/2 |
| 2002/0161385 A1 * | 10/2002 | Wiener et al. ................. | 606/169 |
| 2003/0204199 A1 * | 10/2003 | Novak et al. .................. | 606/169 |
| 2005/0222652 A1 * | 10/2005 | Mori .............................. | 607/105 |
| 2007/0219540 A1 * | 9/2007 | Masotti et al. ................. | 606/3 |
| 2009/0138027 A1 * | 5/2009 | Lucas et al. ................... | 606/132 |
| 2010/0022919 A1 * | 1/2010 | Peterson ........................ | 601/2 |
| 2010/0049178 A1 * | 2/2010 | Deem et al. .................... | 606/9 |

FOREIGN PATENT DOCUMENTS

WO     WO 01/32091    * 10/2001

OTHER PUBLICATIONS

BioHorizons. "AlloDerm Regenerative Tissue Matric" Nov. 15, 2008. <http://www.biohorizons.com/documents/MLD102.pdf>.*
Definition of 'support' from https://www.TheFreeDictionary.com.*
Definition of 'support' from https://www.merriam-webster.com.*
"Indirect contact" definition from <http://medical-dictionary.thefreedictionary.com/indirect+contact> accessed on Jun. 24, 2015.*
Bond et al., "Physics of Ultrasonic Surgery Using Tissue Fragmentation, Part II," *Ultrasound in Med. & Biol.*, 22 (1): 101-117(1996).
Ceccaldi at al, "Apport du bistouri à ultrasons dans la reconstruction mammaire autologue par lambeau de grand dorsal," *J. Gynecol. Obstet. Biol. Reprod.*, 35 (1):762-766 (2006).

(Continued)

*Primary Examiner* — Katherine M Shi
(74) *Attorney, Agent, or Firm* — McCarter & English, LLP; Matthew R. Van Eman

(57) ABSTRACT

Methods for dissecting tissues are provided. The methods comprise selecting a tissue site comprising dermis and subdermal fat connected to the dermis, and applying ultrasonic energy to the tissue to remove at least a portion of the subdermal fat from the dermis, wherein the ultrasonic energy is applied to minimize damage to the dermis.

9 Claims, 1 Drawing Sheet

(56) References Cited

OTHER PUBLICATIONS

Cimino, "The Physics of Soft Tissue Fragmentation Using Ultrasonic Frequency Vibration of Metal Probes," *Clinics in Plastic Surgery.* 26 (3): 447-461 (1999).

Cimino et al., "Physics of Ultrasonic Surgery Using Tissue Fragmentation: Part I," *Ultrasound in Med. & Biol.*, 22 (1): 89-100 (1996).

Cinimo, "Ultrasonic Surgery: Power Quantification and Efficiency Optimization," *Aesthetic Surgery J.*, 21 (3):233-241 (2001).

Hoyos et al., "VASER-Assisted High-Definition Liposculpture," *Aesthetic Surg. J.*, 27:594-604 (2007).

Jewell et al., "Clinical Application of VASER-assisted Lipoplasty: A Pilot Clinical Study," *Aesthetic Surgery J.*, 22:131-146 (2002).

Lee et al., "Ultrasonic Energy in Endoscopic Surgery," *Yonesi Medical J.*, 40 (6): 545-549 (1999).

\* cited by examiner

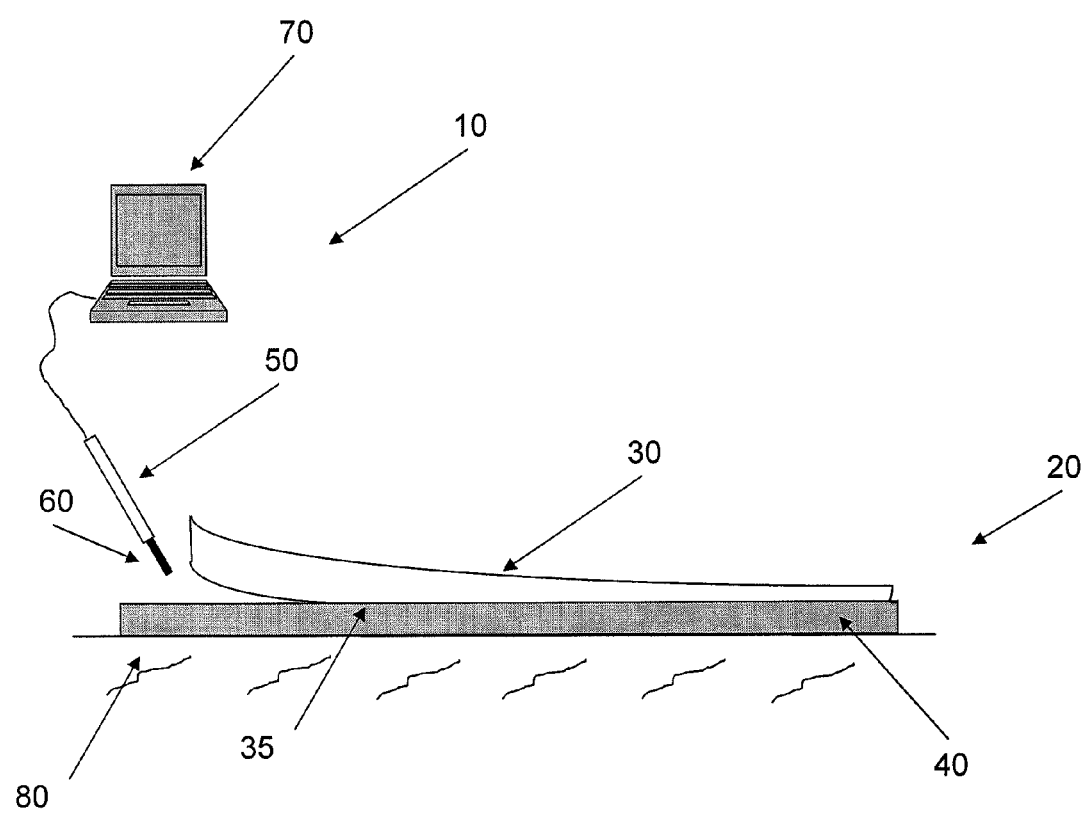

METHOD FOR ULTRASONIC DISSECTION OF TISSUES

This application claims priority under 35 U.S.C. §119 to U.S. Provisional Application No. 61/368,354, which was filed on Jul. 28, 2010, and is hereby incorporated by reference.

Human and animal tissues can be used to produce a variety of tissue products for patient use. When tissues are procured from tissue banks or animal sources, the tissues must be separated from unnecessary or undesired adjacent tissues. However, separation of certain tissues can be time consuming and difficult. In addition, the desired tissue components can be damaged during the separation process, especially if sharp instruments or high-energy devices are used.

Accordingly, there is a need for improved methods for dissecting tissues that can be used in production of medical devices, such as acellular tissue matrices.

SUMMARY

According to certain embodiments, a method for dissecting tissues is provided. The method comprises selecting a tissue site comprising dermis and subdermal fat connected to the dermis, and applying ultrasonic energy to the tissue to remove at least a portion of the subdermal fat from the dermis, wherein the ultrasonic energy is applied to minimize damage to the dermis.

DESCRIPTION OF THE DRAWINGS

FIG. 1 illustrates a device for dissecting tissues to remove subdermal fat from dermis, according to certain embodiments.

DESCRIPTION OF CERTAIN EXEMPLARY EMBODIMENTS

Reference will now be made in detail to the certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Human and animal tissues can be used to produce a variety of tissue products for patient use. For example, human and animal dermis can be used to produce a variety of useful medical devices or tissue products. Such products can include, for example, reconstituted skin grafts and acellular tissue matrix products. Examples of such acellular tissue matrix products include ALLODERM®, which is a freeze-dried acellular human dermal tissue matrix, CYMETRA®, a particulate acellular human dermal tissue matrix, and STRATTICE™, a porcine acellular dermal matrix, all of which are produced by LifeCell Corporation, Branchburg, N.J.

When tissues are procured from tissue banks or animal sources, the tissues must be separated from unnecessary or undesired adjacent tissues. For example, dermis is naturally attached to underlying fat and/or other tissues, which must be removed to produce dermal products such as acellular tissue matrices. However, dissecting subdermal fat free from dermis can be difficult and time consuming. In addition, typical methods for removal of fat, such as cutting with relatively sharp instruments, can damage the desired dermal materials, thereby making the materials less suitable for their intended use. Development of methods for faster, more reliable removal of subdermal fat from dermis are needed.

The present disclosure provides a method for dissecting tissues. As used herein "dissecting tissues" will refer to separating tissues that are connected into two pieces. "Dissecting tissues" does not necessarily mean that two tissue types, e.g., fat and dermis, are perfectly separated along an actual tissue plane. In certain embodiments, the method includes selecting a tissue site comprising dermis and subdermal fat connected to the dermis. Ultrasonic energy is applied to the tissue to remove at least a portion of the subdermal fat from the dermis, wherein the ultrasonic energy is applied to minimize damage to the dermis.

In certain embodiments, all or part of the subdermal fat is removed. For example, in order to provide tissues suitable for production of acellular tissue matrices or other products, it may be desirable to remove all or nearly all the subdermal fat. However, removal of the fat that is very close to the dermis may increase the risk of damage to the dermis through mechanical or thermal means. Accordingly, in some embodiments, the ultrasonic energy is applied to remove most of the fat, but it will be understood that a small amount of fat may remain. Thus, in certain embodiments, at least 70%, 80%, 90%, 95%, 99%, 99.5% (or any value inbetween) of the subdermal fat is removed from the dermis.

The ultrasonic energy may be applied using a number of different ultrasonic delivery systems. FIG. 1 illustrates a device 10 for dissecting tissues 20 to remove subdermal fat 30 from dermis 40, according to certain embodiments. As shown, the device includes an ultrasound probe 50 with a tip 60 that delivers energy to subdermal fat 30 or a dermal-fat junction 35. The ultrasound probe will include an ultrasonic actuator (e.g., a piezoelectric actuator), which can be controlled by an energy control system 70 to control various ultrasound process parameters.

The method of dissecting can be performed on tissue that is present on a human cadaver or animal or on tissue that has been separated from the cadaver or animal source. For example, in some embodiments, the subdermal fat and dermis have been cut free of a cadaver to form a sheet of tissue 20. As shown in FIG. 1, the sheet 20 can be laid flat on a cooling surface 80 during dissection. Ultrasonic energy is passed through a probe to the dermal-subdermal fat junction. Subdermal fat is rapidly separated from dermis while keeping the dermal temperature below 50° C. (e.g., by contact with a cooling surface or cold fluid). In another example, the dermis and subdermal fat are not removed from a cadaver. The cadaver can be in contact with a cold fluid or wrapped in a cooling jacket or other flexible structure during dissection to prevent heating the dermis above 50° C. Ultrasonic energy is passed through a probe to the dermal-subdermal fat junction. Dermis is rapidly separated from subdermal fat on the cadaver.

Various ultrasound process parameters can be controlled to optimize the dissection process. For example, certain parameters can be modified to improve speed, reduce heat generation/control heating of dermal tissue, and/or to improve fat removal. For instance, in various embodiments, the probe amplitude, frequency, tip area, probe shape, electrical waveform (continuous or pulsed) can be controlled. In certain embodiments, a blunt probe is used. In some embodiments, the ultrasound properties are selected such that the energy selectively fragments fat without fragmenting dermis.

Typical frequencies for ultrasonic dissection tools are 20-60 kHz. However, those frequencies and power densities are generally used for surgical applications on patients. The frequencies and power densities may be varied for dissection of tissues on cadavers or for tissues which have been removed from cadavers in order to optimize cutting speed, and/or reduce or prevent damage to dermal tissue, as desired. In various embodiments, high power densities (e.g., higher than may be used on a living patient) can be used to speed tissue dissection. The higher power densities may be possible due to cooling of the tissue before and/or during dissection, thereby preventing thermal damage. In various embodiments, ultrasonic frequencies of at least 20 kHz are used to dissect dermis from subdermal fat. In further embodiments, at least 40 kHz, at least 60 kHz, at least 70 kHz, at least 80 kHz, at least 90 kHz, or at least 100 kHz frequencies are used. In certain embodiments, the use of frequencies above 60 kHz enables faster dissection of subdermal fat from dermis than would be possible in dissection from a living tissue host.

In yet further embodiments, cooling is used to keep the temperature of the dermis and subdermal fat below 50° C. when using the at least 40 kHz, at least 60 kHz, at least 70 kHz, at least 80 kHz, at least 90 kHz, or at least 100 kHz ultrasonic frequencies. In still further embodiments, the cooling is by irrigation with a cooling fluid. In still further embodiments, when the tissue is still attached to a cadaver, cooling can be performed by passing cooling fluid through a cooling jacket or other flexible structure laid on and/or under the cadaver. In other embodiments, where the dermis and subdermal fat have been removed from the cadaver prior to dissection of subdermal fat, cooling can be performed by laying the tissue on a cooling surface.

The ultrasonic energy may be configured to dissect fat using a variety of mechanisms. For example, in various embodiments, the ultrasonic energy is applied to cut, melt, or emulsify fat. In certain embodiments, the probe size, width, and shape are selected to optimize the desired dissection method (e.g., a sharp/wide probe may be used for cutting subdermal fat from dermis while delivering ultrasonic energy along a wide surface area to increase the speed of dissection). In certain embodiments, the probe is capable of delivering ultrasonic energy of variable frequencies and power densities to the dermal-subdermal fat junction. In further embodiments, the probe is capable of delivering at least 40 kHz, at least 60 kHz, at least 70 kHz, at least 80 kHz, at least 90 kHz, or at least 100 kHz ultrasonic frequencies. In various embodiments, a wide probe is used to deliver ultrasonic energy across a wide surface area. In further embodiments, the wide surface area serves to increase the speed of dissection by emulsifying or melting more fat simultaneously across the wide surface area. In still further embodiments, a wide, blunt probe is used. The wide, blunt probe emulsifies and/or melts fat immediately in front of the probe, allowing the probe to continue advancing rapidly along the plane of the dermis-subdermal fat junction until the dermis has been fully separated from the subdermal fat.

Ultrasonic dissection tools can generate heat, and in some embodiments, may be configured to melt subdermal fat to assist in fat removal. However, excessive heating may damage the adjacent dermis, thereby making part of the dermis unsuitable for use as an acellular tissue matrix or other tissue product. Accordingly, in certain embodiments, the ultrasonic energy is applied to remove fat without causing excessive heating of the dermis. In various embodiments, the dermis reaches a maximum temperature and heating time that does not damage the dermal extracellular matrix of the skin. In further embodiments, the dermis is substantially undamaged by ultrasonic heating during separation of subdermal fat, as compared to un-harvested dermis (i.e., the dermis retains most of the physiological properties and structural integrity of un-harvested dermis). In certain embodiments, either a portion or all of the dermis is heated to no more than 50° C., no more than 45° C., or no more than 40° C. (or any temperature inbetween). Further, the degree of heating that is permissible may vary based on the tissue source (e.g., human versus pig) and the intended application. Accordingly, in various embodiments, the temperature is controlled to prevent heating of any or part of the dermis that may cause unacceptable alteration in collagen or other extracellular matrix proteins (e.g., by causing excessive denaturation or other damage).

In some embodiments, to prevent excessive heating of dermis while allowing rapid removal of fat, the dermis may be cooled during application of the ultrasonic energy. In certain embodiments, the dermis is cooled prior to application of ultrasonic energy, e.g., the dermis is cooled to at or near freezing temperatures. Cooling can be effectuated in a number of ways. For example, in some embodiments, cooling is performed by contacting the dermis with a cold surface 80, as shown in FIG. 1. Contact with the cold surface establishes a thermal gradient through the dermal tissue, cooling the tissue as it is heated by the ultrasonic energy, and thereby preventing the dermis from burning when ultrasonic energy is applied. In other embodiments, e.g., when the tissue is still attached to a cadaver or animal, the dermis may be cooled by irrigating the epidermal side of the tissue with cooling fluid, and/or supplying irrigation to the ultrasound probe site. In addition, cooling fluid may be provided using a cooling jacket, wherein a cooled fluid is passed through a flexible structure that can be laid on or under the dermis to continuously cool the tissue during application of ultrasonic energy. In some embodiments, all or part of the tissue is frozen before application of ultrasonic energy.

What is claimed is:

1. A method for dissecting tissues, comprising:
    selecting tissue removed from a cadaver or animal source, the tissue comprising dermis and subdermal fat connected to the dermis;
    applying ultrasonic energy to the removed tissue to remove at least a portion of the subdermal fat from the dermis, wherein the ultrasonic energy is pulsed, and wherein the ultrasonic energy is applied to minimize damage to the dermis; and
    cooling the dermis while applying the ultrasonic energy, wherein the cooling is performed by laying the dermis upon a solid supporting cold surface.

2. The method of claim 1, wherein at least a portion of the dermis is not heated to greater than 50° C.

3. The method of claim 2, wherein the entire dermis is not heated to greater than 50° C.

4. The method of claim 1, wherein the ultrasonic energy is applied with a blunt probe.

5. The method of claim 1, wherein the ultrasonic energy is applied at a dermal-fat junction.

6. The method of claim 1, wherein the ultrasonic energy is applied to cut, melt, or emulsify fat.

7. The method of claim 1, wherein the dermis is human dermis.

8. The method of claim 1, wherein substantially all the subdermal fat is removed from the dermis.

9. The method of claim 1, wherein the cooling is performed by contacting the dermis with a cold surface applied to an entire surface of the tissue site.

\* \* \* \* \*